United States Patent
Ho et al.

(10) Patent No.: US 9,194,822 B2
(45) Date of Patent: Nov. 24, 2015

(54) ADJUSTABLE FIXTURE STRUCTURE FOR 3-DIMENSIONAL X-RAY COMPUTED TOMOGRAPHY

(71) Applicant: YUAN ZE UNIVERSITY, Taoyuan (TW)

(72) Inventors: Cheng-En Ho, Taoyuan (TW);
Cheng-Hsien Yang, Taoyuan (TW);
Ling-Huang Hsu, Taoyuan (TW)

(73) Assignee: YUAN ZE UNIVERSITY, Taoyuan (TW)

( * ) Notice: Subject to any disclaimer, the term of this patent is extended or adjusted under 35 U.S.C. 154(b) by 232 days.

(21) Appl. No.: 14/106,867

(22) Filed: Dec. 16, 2013

(65) Prior Publication Data

US 2015/0168316 A1    Jun. 18, 2015

(51) Int. Cl.
*G01N 23/00* (2006.01)
*G01N 23/04* (2006.01)

(52) U.S. Cl.
CPC ........ *G01N 23/046* (2013.01); *G01N 2223/307* (2013.01); *G01N 2223/309* (2013.01)

(58) Field of Classification Search
CPC ...... A61B 6/032; A61B 6/035; G01N 23/046; G01N 23/083; G01N 23/20025; G01N 23/2204; G01N 2223/307; G01N 2223/309; G01N 2223/321; G01N 2223/3303; G01N 2223/3306; G21K 5/08
See application file for complete search history.

(56) References Cited

U.S. PATENT DOCUMENTS

| | | | | |
|---|---|---|---|---|
| 3,723,006 A | * | 3/1973 | Thomas, Jr. | G01N 23/20025 269/21 |
| 8,604,445 B2 | * | 12/2013 | Yamazaki | H01J 37/26 250/440.11 |
| 2011/0253905 A1 | * | 10/2011 | Moebus | G21K 7/00 250/441.11 |
| 2012/0025103 A1 | * | 2/2012 | Deshmukh | G01N 21/0303 250/491.1 |
| 2012/0293791 A1 | * | 11/2012 | Milas | H01J 37/20 356/72 |
| 2013/0014528 A1 | * | 1/2013 | Stabacinskiene | G01N 23/20033 62/129 |
| 2015/0168316 A1 | * | 6/2015 | Ho | G01N 23/046 378/20 |

FOREIGN PATENT DOCUMENTS

| | | | | |
|---|---|---|---|---|
| DE | WO 2013005180 A1 | * | 1/2013 | ....... G01N 23/20033 |
| DE | 202013003922 U1 | * | 5/2013 | ........... G01N 23/046 |
| DE | 102015101378 A1 | * | 7/2015 | ............. G01B 15/04 |
| FR | 2990025 A1 | * | 11/2013 | ........... G01N 23/046 |

* cited by examiner

*Primary Examiner* — Thomas R Artman
(74) *Attorney, Agent, or Firm* — Chih Feng Yeh; Huntington IP Consulting Co., Ltd.

(57) ABSTRACT

An adjustable fixture structure for a 3D X-ray CT device is disclosed. Only the detected article is fixed on the fixture element of the adjustable fixture structure, may the adjustable connecting element slide with respect to the adjustable sliding trough and the fixture element slide with respect to the fixture sliding trough, so that the detected article is adjusted into within the detection range of the 3D X-ray CT device by using the adjustable connecting element and the fixture element. As such, the issues which a detected article is difficult to be oriented and positioned, a detection efficacy and result is poor, and the detected article might thus be damaged, may be well overcome.

10 Claims, 6 Drawing Sheets

ADJUSTABLE FIXTURE STRUCTURE FOR 3-DIMENSIONAL X-RAY COMPUTED TOMOGRAPHY

BACKGROUND OF THE RELATED ART

1. Technical Field

The present invention is related to a fixture structure, and particularly to an adjustable fixture structure for used in a 3-dimensional X-ray computed tomography device.

2. Related Art

A 3-dimensional X-ray computed tomography (3D X-ray CT) device is a device commonly for displaying an internal structure of an article. In observing, a non-violating X-ray is emitted to see through the article to be detected fixed on a fixture. To detect the article from different directions and angles, the fixture has to be rotated, generally for 360 degrees. Then, an image acquiring device (e.g. charge-coupled device, CCD) is employed to collect the see-through images obtained from different directions and angles. Finally, a computer software is used to reconstruct a 3D image of the article. In this manner, a tomography analysis for a detected article (or specimen) is possible.

Although the 3D X-ray CT device may be widely used and thus practicable, it is still currently to be further addressed for the orientation of the detected article since the see-through images of the X-ray collected from the image acquiring device is closely related to how accurate the orientation of the detected article is. If the detected article deviates from its accurate position, the see-through images collected from the image acquiring device are not correct and complete. And this situation may become worse when the resulted 3D image is magnified.

When the 3D image is magnified, only a small deviation may, as mentioned, cause failure of the image acquiring device for getting complete see-through images for the resulting 3D image. For the currently available, the orientation task of the detected article is performed by manually detaching the detected article from the fixture and then repeatedly adjusting the orientation and position of the article. However, this manner not only wastes time but also cause an inaccuracy of the orientation and positioning of the detected article. Worse yet, a precise article may suffer a possibility of careless damage on the course of being detached from the fixture.

In view of the above, there is a long need for an improved technique for orientation and positioning of the detected article used in a 3D X-ray CT device due to the above mentioned issues.

SUMMARY

To improve the prior art of a fixture structure used in a 3D X-ray computed tomography (CT) device where a detected article is difficult to be positioned, a detection efficacy and result is poor, and the detected article might be damaged, the present invention discloses a fixture structure for a 3D X-ray CT device.

The adjustable fixture structure for a 3D X-ray CT device according to the present invention comprises a connecting bottom base, an adjustable connecting element, a fixture element, a first screw element, and a second screw element.

The connecting bottom base has a top end, a bottom end, a bottom face, an adjustable sliding trough and a first inner screw thread, the adjustable sliding trough having a bottom face and being disposed on the top end thereof, the first inner screw thread being disposed within the bottom face thereof and extending through the bottom face of adjustable sliding trough, and the bottom end of the connecting bottom base fixing the adjustable fixture structure on the 3D X-ray CT device;

The adjustable connecting element has a bottom end and a connection mating portion having a shape and dimension mating with a shape and dimension of the adjustable sliding trough, so that the adjustable connecting element is disposed on the connecting bottom base and slides with respect to the adjustable sliding trough, the adjustable connecting element having a top end and a fixture sliding trough disposed thereon, the fixture sliding trough having a sliding direction in perpendicular with a sliding direction of the adjustable sliding trough, the side face of adjustable connecting element having a penetrating trough running therethrough and having a top face, and an adjustable connecting element having a second inner screw thread therein runs through the top face of the penetrating trough and the bottom face of the fixture sliding trough;

The fixture element has a top end having a side face and a bottom end, and a fixture mating portion disposed on the bottom end thereof, the fixture mating portion having a shape and dimension mating a shape and dimension of the fixture sliding trough, so that the fixture element is disposed on the adjustable connecting element and slides with respect to the fixture sliding trough, the fixture element having a fixture trough and a plurality of fixing portions disposed at the side face of the top end of the fixture element, wherein a detected article having a detection fixing portion is disposed within the fixture trough and fixed by a proper one among the plurality of fixing portions;

The first screw element is threaded from the bottom face of the connection bottom base into the first inner screw thread within the connecting bottom base, wherein in a detecting task for the detected article by using the 3D X-ray CT device, the adjustable connecting element slides with respect to the adjustable sliding trough and the fixture element slides with respect to the fixture sliding trough, so that the detected article is adjusted into within a detection range by using the adjustable connecting element and the fixture element, so as to fix the adjustable connecting element.

The second screw element is threaded from the top face of the penetrating trough into the second inner screw thread within the adjustable connecting element, wherein in the detecting task for the detected article by using the 3D X-ray CT device, the adjustable connecting element slides with respect to the adjustable sliding trough and the fixture element slides with respect to the fixture sliding trough, so that the detected article is adjusted into within the detection range by using the adjustable connecting element and the fixture element, so as to fix the fixture element.

The present invention has the difference, compared with the prior art, residing in that only the detected article is fixed on the fixture element of the adjustable fixture structure, may the adjustable connecting element slide with respect to the adjustable sliding trough and the fixture element slide with respect to the fixture sliding trough, so that the detected article is adjusted into within the detection range of the 3D X-ray CT device by using the adjustable connecting element and the fixture element. As such, the issues which a detected article is difficult to be oriented and positioned, a detection efficacy and result is poor, and the detected article might thus be damaged, may be well overcome.

By implementing the above technique, the present invention may readily provide an adjustable fixture for a 3D X-ray CT device which may achieve the result of convenient orientation and positioning and avoidance of damage of the detected article.

BRIEF DESCRIPTION OF THE DRAWINGS

The invention will become more fully understood from the detailed description given herein below illustration only, and thus is not limitative of the present invention, and wherein.

DETAILED DESCRIPTION

The present invention will be apparent from the following detailed description, which proceeds with reference to the accompanying drawings, wherein the same references relate to the same elements. With reference to the detailed description, those skilled in the art may use the technical skill to solve the associated problem and thus achieve in the technical efficacy associated therewith, namely, may be enabled to implement the present invention.

Figure 1:
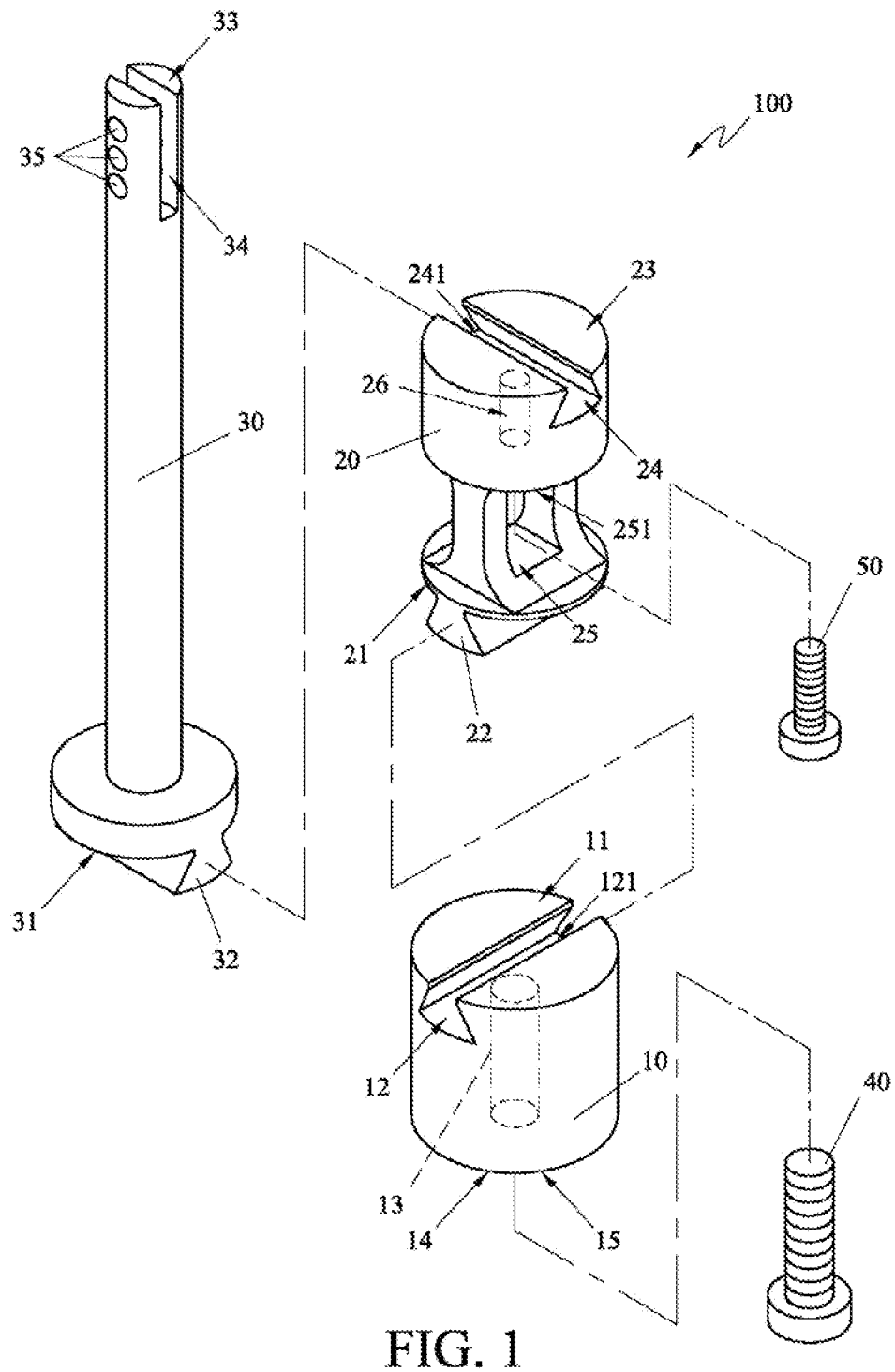
FIG. 1 is an exploded diagram of an illustration of an adjustable fixture structure for a 3D X-ray computed tomography (CT) device according to the present invention.

In the description follows as below, an adjustable fixture structure for a 3D X-ray computed tomography (CT) device disclosed in the present invention will be explained. Referring first to FIG. 1, an exploded diagram of an adjustable fixture structure for a 3D X-ray CT device according to the present invention is illustrated therein.

The adjustable fixture structure comprises a connecting bottom base 10, an adjustable connecting element 20, a fixture element 30, a first screw element 40, and a second screw element 50.

At a top end 11 of the connecting bottom base 10, there is an adjustable sliding trough 12 disposed. Within the connecting bottom base 10, a first inner screw thread 13 runs from the connecting bottom base 10 through a bottom face 121 of the adjustable sliding trough 12. Further, a bottom end 15 fixes the adjustable fixture structure 100 on the 3D X-ray CT device by using a threading or snapping manner, which are only examples, but not to limit the present invention. The connecting bottom base 10 is made of a metal, such as copper and iron, which are only examples, not to limit the present invention, or a thermoplastic polymer material, such as PP and PVC, which are only examples, not to limit the present invention.

It is to be noted that the adjustable sliding trough 12 in FIG. 1 is shown with the connecting bottom base 10 supporting the adjustable sliding trough 12 at its top end 11, as having a trapezoid with a neck portion, which is only an example, not to limit the present invention. In fact, the adjustable sliding trough 12 may also take the shape of rectangular having a neck portion, circle having a neck portion, or diamond having a neck portion. The mentioned neck portion is used to limit a sliding direction along which the adjustable connecting element 20 with respect to the connecting bottom base 10. It means that the adjustable connecting element 20 may only slide along the adjustable sliding trough 12.

The adjustable connecting element 20 has a connection mating portion 22 at its bottom end 21. The connection mating portion 22 has a shape and dimension mating with a shape and dimension of the adjustable sliding trough 12, i.e. the above mentioned trapezoid having a neck portion, rectangular having a neck portion, circle having a neck portion, or diamond having a neck portion, which are also examples, not to limit the present invention. As such, the adjustable connecting element 20 is disposed on the connecting bottom base 10 and slides along with the adjustable sliding trough 12 with respect to the connecting bottom base 10.

Further, the adjustable element 20 has a fixture sliding trough 24 disposed at its top end 23. The fixture sliding trough 24 has a sliding direction in perpendicular with that of the adjustable sliding trough 12. At a side face of the adjustable connecting element 20, a penetrating trough 25 runs therethrough. Inside the adjustable connection element 20, a second inner screw thread 26 runs through a top face 251 of the penetrating trough 25 and a bottom face 241 of the fixture sliding trough 24. The adjustable connecting element 20 is also made of a metal, such as copper and iron, which are only examples, not to limit the present invention, or a thermoplastic polymer material, such as PP and PVC, which are only examples, not to limit the present invention.

It is to be noted that the fixture sliding trough 24 disposed on the top end 23 of the adjustable connecting element 20 is illustrated as having a trapezoid shape having a neck portion, but it is only an example, not a limitation of the present invention. The sliding trough 24 may, in fact, also take a shape of rectangular having a neck portion, circle having a neck portion, and diamond having a neck portion. The mentioned neck portion is used to limit a sliding direction of the fixture element 30 with respect to the adjustable connecting element 20. Namely, the fixture element 30 may only slide along the fixture sliding trough 24 of the adjustable connecting element 20, which is in perpendicular with that of the adjustable sliding trough 12 of the connecting bottom base 10.

The fixture element 30 has a fixture mating portion 32 disposed at its bottom end 31. The fixture mating portion 32 has a shape and dimension mating with a shape and dimension of the fixture sliding trough 24, so that the fixture element 30 is disposed on the adjustable connecting element 20 and slides along with the fixture sliding trough 24 with respect to the adjustable connecting element 20. Namely, the fixture mating portion 32 takes a shape of trapezoid having a neck portion, rectangular having a neck portion, circle having a neck portion, and diamond having a neck portion, but which are also examples, not to limit the present invention.

The fixture element 30 has a fixture trough 34 and a plurality of fixing portions 35 disposed at a top end 33 thereof, in which the fixing portions 35 are disposed at a side face of the top end 33 of the fixture element 30. The fixture element 30 is also made of a metal, such as copper and iron, which are only examples, not to limit the present invention, or a thermoplastic polymer material, such as PP and PVC, which are only examples, not to limit the present invention.

The first screw element 40 is threaded into the first inner screw thread 13 within the bottom face 14 of the connecting bottom base 10. Further, the first screw element 40 provides a fixation of the adjustable connecting element 20 by giving a pressure after the adjustable connecting element 20 slides along the adjustable sliding trough 12 of the connecting bottom base 10.

The second screw element 50 is threaded from the top face of the penetrating trough 25 into the second inner screw thread 26 within the adjustable connecting element 20. Further, the second screw element 50 provides a fixation of the fixture element 30 by giving a pressure after the fixture element 30 slides along the fixture sliding trough 24 of the adjustable connecting element 20.

Figure 2:
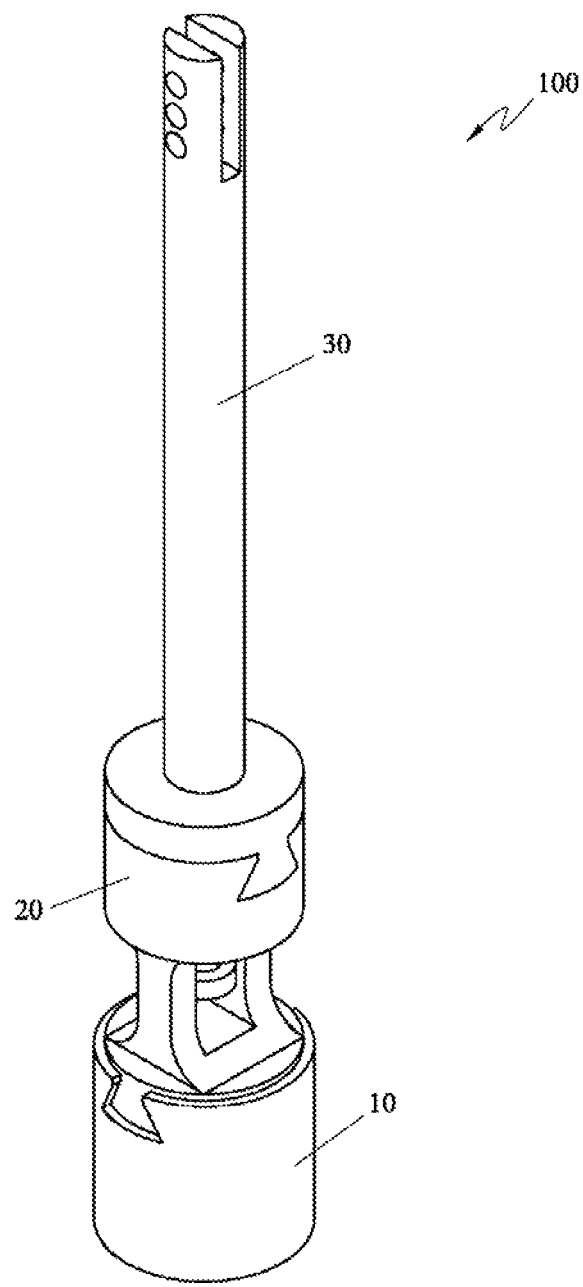
FIG. 2 is a 3D diagram of an illustration of the adjustable fixture structure for a 3D X-ray CT device according to the present invention.

When the above mentioned connecting bottom base 10, adjustable connecting element 20, fixture element 30, first screw element 40 and second screw element 50 are assembled and fixed jointly, the adjustable fixture structure 100 for a 3D X-ray CT device is thus obtained, which is schematically shown in FIG. 2.

Figure 3A:
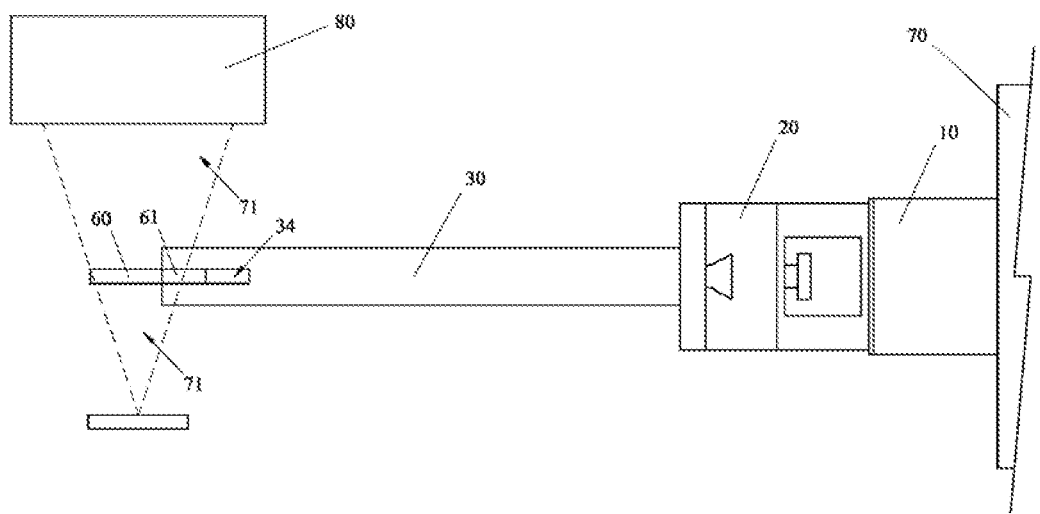
FIG. 3A is a side-view diagram of an illustration of the adjustable fixture structure for a 3D X-ray CT device from a first viewing angle according to the present invention.
Figure 3B:
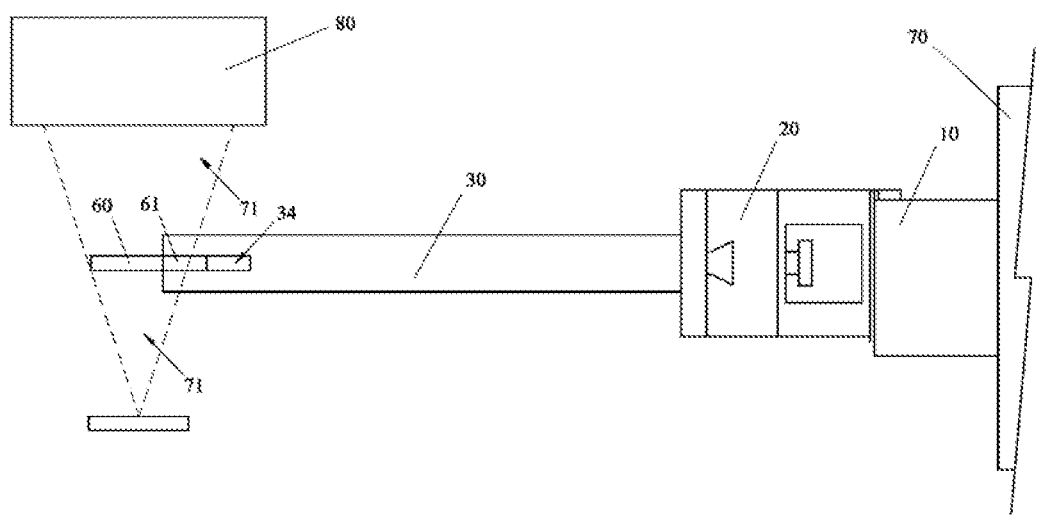
FIG. 3B is a side-view diagram of an illustration of a state of the adjustable fixture structure for a 3D X-ray CT device from the first viewing angle when an adjustable connecting element is completely adjusted according to the present invention.

Thereafter, referring to FIG. 3A and FIG. 3B, in which a side-view diagram for illustrating the adjustable fixture structure for a 3D X-ray CT device from a first viewing angle according to the present invention, and a side-view diagram of an illustration of a state of the adjustable fixture structure for a 3D X-ray CT device from the first viewing angle when the adjustable connecting element 20 is completely adjusted according to the present invention, are shown, respectively.

A detected article 60 has a plurality of detection fixing portions 61, disposed within a fixture trough 34 of the fixture element 30 and fixed by a proper one of the fixing portions 35 by using a threading manner. That is, the different fixing portions 35 are jointly used to properly lay a detection position of the detected article 60 on the fixture element 30. When the detected article 60 is fixed on the fixture element 30, the adjustable fixture structure 100 is fixed on the 3D X-ray CT device 70.

In detecting the detected article 60 by using the 3D X-ray CT device 70, since the device 70 has a conical-shaped detection range 71, it may be apparently found from FIG. 3A that when the detected article 60 is not totally covered by the conical-shaped detection range 71, the 3D image obtained by reconstruction of the detected article 60 is lack of accuracy as compared to the detected article 60. At this time, the first screw element 40 is loosened to let the adjustable connecting element 20 slide with respect to the adjustable sliding trough 12 of the connecting bottom base 10 to adjust the detected article 60. As such, the X-axle position of the detected article 60 is moved, which is only an example, not to limit the present invention. The detected article 60 is moved so that the detected article 60 may be entirely covered by the conical-shaped detection range 71. The adjusted result of the adjustable connecting element 20 with respect to the connecting bottom base 10 may be seen in FIG. 3B. Further, the adjustable connecting element 20 may be fixed again by using the first screw element 40.

After the adjustable connecting element 20 slides with respect to the adjustable sliding trough 12 of the connecting bottom base 10 to adjust the detected article 60 to fall entirely within the detection range 71 of conical shape, the 3D X-ray CT device 70 causes the adjustable fixture structure 100 to rotate by 360 degrees to get see-through images obtained from each direction and angle of the detected article 60 by an image acquiring device 80. As such, a 3D image of the detected article 60 is reconstructed by referring to all the see-through images.

Figure 4A:
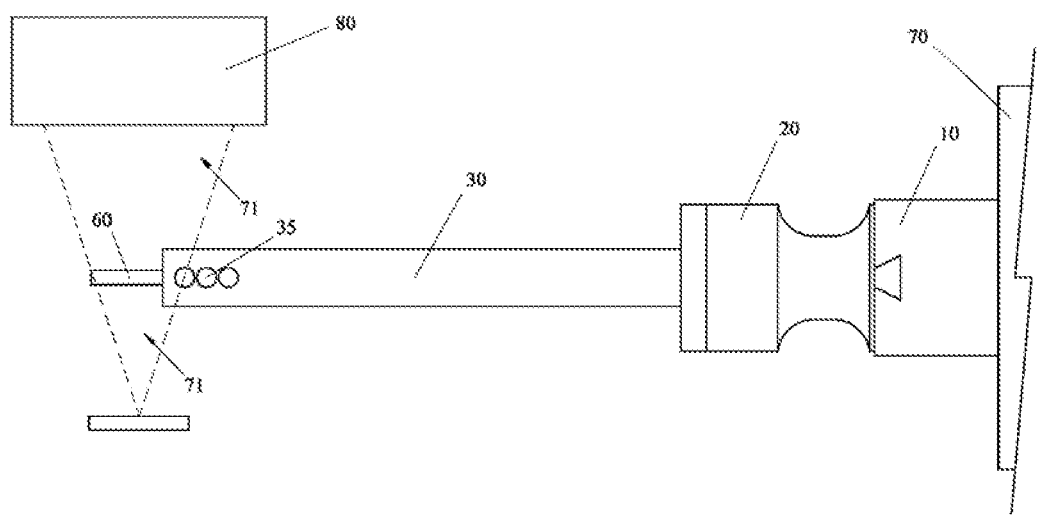
FIG. 4A is a side-view diagram of an illustration of the adjustable fixture structure for a 3D X-ray CT device from a second viewing angle according to the present invention.
Figure 4B:
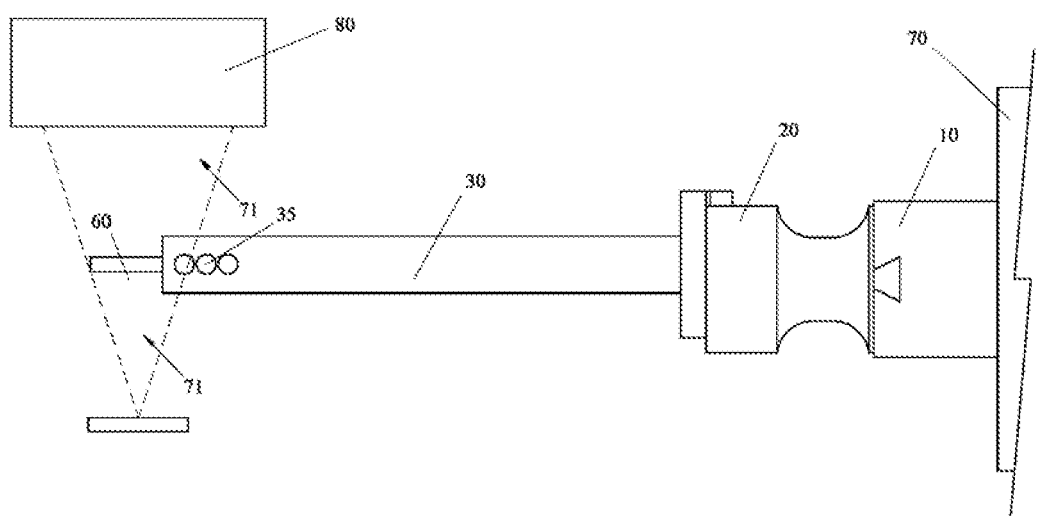
FIG. 4B is a side-view diagram of an illustration of a state of the adjustable fixture structure for a 3D X-ray CT device from the second viewing angle when a fixture element is completely adjusted according to the present invention.

Referring next to FIGS. 4A and 4B, in which a side-view diagram for illustrating the adjustable fixture structure for a 3D X-ray CT device from a second viewing angle according to the present invention, and a side-view diagram for illustrating a state of the adjustable fixture structure for a 3D X-ray CT device from the second viewing angle when the fixture element is completely adjusted according to the present invention, are shown, respectively.

The detection fixing portions 61 of the detected article 60 are disposed within the fixture trough 34 of the fixture element 30, and the detected article 60 is fixed by a proper one among the detection fixing portions 35 by a threading manner. That is, the different fixing portions 35 are jointly used to properly lay a detection position of the detected article 60 on the fixture element 30. When the detected article 60 is fixed on the fixture element 30, the adjustable fixture structure 100 is fixed on the 3D X-ray CT device 70.

In detecting the detected article 60 by using the 3D X-ray CT device 70, since the device 70 has a conical-shaped detection range 71, it may be apparently found from FIG. 4A that when the detected article 60 is not entirely covered by the conical-shaped detection range 71, the 3D image obtained by reconstruction of the detected article 60 is lack of accuracy as compared to the detected article 60.

At this time, the second screw element 50 is loosened to let the fixture element 30 slide with respect to the fixture sliding trough 24 of the adjustable connecting element 20 to adjust the detected article 60. As such, the Y-axle position of the detected article 60 is adjusted and moved, which is only an example, not to limit the present invention. The detected article 60 is moved so that the detected article 60 may be entirely covered by the conical-shaped detection range 71. The adjusted result of the fixture element 30 with respect to the adjustable connecting element 20 may be seen in FIG. 4B. Further, the fixture element 30 may be fixed again by using the second screw element 50.

After the fixture element 30 slides with respect to the fixture sliding trough 24 of the adjustable connecting element 20 to adjust the detected article 60 to fall entirely within the detection range 71 of conical shape, the 3D X-ray CT device 70 causes the adjustable fixture structure 100 to rotate by 360 degrees to get see-through images obtained from each direction and angle of the detected article 60 by an image acquiring device 80. As such, a 3D image of the detected article 60 is reconstructed by referring to all the see-through images.

Alternatively, the adjustable connecting element 20 and the fixture element 30 may concurrently slide with respect to the adjustable sliding trough 12 of the connecting bottom base 10 and the fixture sliding trough 24 of the adjustable connecting element 20, respectively, to adjust the detected article 60 to fall entirely within the detection range 71 of conical shape, instead of the single sliding of the adjustable connecting element 20 or the fixture element 30, mentioned respectively above. In this manner, the 3D X-ray CT device 70 also causes the adjustable fixture structure 100 to rotate by 360 degrees to get see-through images obtained from each direction and angle of the detected article 60 by an image acquiring device 80. As such, a 3D image of the detected article 60 is reconstructed by referring to all the see-through images.

In summary, the present invention has the difference, compared with the prior art, residing in that only the detected article is fixed on the fixture element of the adjustable fixture structure, may the adjustable connecting element slide with respect to the adjustable sliding trough and the fixture element slide with respect to the fixture sliding trough, so that the detected article is adjusted into within the detection range of the 3D X-ray CT device by using the adjustable connecting element and the fixture element. As such, the issues which a detected article is difficult to be oriented and positioned, a detection efficacy and result is poor, and the detected article might thus be damaged, may be well overcome.

By implementing the technique disclosed in the present invention, the issues encountered in the prior art which a detected article is difficult to be oriented and positioned, a detection efficacy and result is poor, and the detected article might thus be damaged, may be well overcome. Moreover, the fixture used for such 3D X-ray CT device may be provided as being easy to be positioned and not easy to be damaged of the detected article.

What is claimed is:

1. An adjustable fixture structure for a 3D X-ray computed tomography (CT) device, comprising:
    a connecting bottom base, having a top end, a bottom end, a bottom face, an adjustable sliding trough and a first inner screw thread, the adjustable sliding trough having a bottom face and being disposed on the top end thereof, the first inner screw thread being disposed within the bottom face thereof and extending through the bottom face of the adjustable sliding trough, and the bottom end of the connecting bottom base fixing the adjustable fixture structure on the 3D X-ray CT device;
    an adjustable connecting element, having a bottom end and a connection mating portion having a shape and dimension mating with a shape and dimension of the adjustable sliding trough, so that the adjustable connecting element is disposed on the connecting bottom base and slides with respect to the adjustable sliding trough, the adjustable connecting element having a top end and a fixture sliding trough disposed thereon, the fixture sliding trough having a sliding direction in perpendicular with a sliding direction of the adjustable sliding trough, the adjustable connecting element having a side face having a penetrating trough running therethrough and having a top face, and an adjustable connecting element having a second inner screw thread therein runs through the top face of the penetrating trough and the bottom face of the fixture sliding trough;
    a fixture element, having a top end having a side face and a bottom end, and
    a fixture mating portion disposed on the bottom end thereof, the fixture mating portion having a shape and dimension mating a shape and dimension of the fixture sliding trough, so that the fixture element is disposed on the adjustable connecting element and slides with respect to the fixture sliding trough, the fixture element having a fixture trough and a plurality of fixing portions disposed at the side face of the top end of the fixture element, wherein a detected article having a detection fixing portion is disposed within the fixture trough and fixed by a proper one among the plurality of fixing portions;
    a first screw element, being threaded from the bottom face of the connection bottom base into the first inner screw thread within the connecting bottom base, wherein in a detecting task for the detected article by using the 3D X-ray CT device, the adjustable connecting element slides with respect to the adjustable sliding trough and the fixture element slides with respect to the fixture sliding trough, so that the detected article is adjusted into within a detection range by using the adjustable connecting element and the fixture element, so as to fix the adjustable connecting element; and
    a second screw element, being threaded from the top face of the penetrating trough into the second inner screw thread within the adjustable connecting element, wherein in the detecting task for the detected article by using the 3D X-ray CT device, the adjustable connecting element slides with respect to the adjustable sliding trough and the fixture element slides with respect to the fixture sliding trough, so that the detected article is adjusted into within the detection range by using the adjustable connecting element and the fixture element, so as to fix the fixture element.

2. The adjustable fixture structure as claimed in claim 1, wherein when the adjustable fixture structure is fixed on the 3D X-ray CT device, the adjustable fixture structure is caused to rotate by 360 degrees by the 3D X-ray CT device so that a plurality of see-through images each corresponding to each angle from the 360 degrees are acquired to reconstruct a 3D image of the detected article.

3. The adjustable fixture structure as claimed in claim 1, wherein the detection range of the 3D X-ray CT device has a conical shape.

4. The adjustable fixture structure as claimed in claim 1, wherein the connecting base bottom is made of one of a metal and a thermo-plastic polymer.

5. The adjustable fixture structure as claimed in claim 1, wherein the adjustable connecting element is made of one of a metal and a thermo-plastic polymer.

6. The adjustable fixture structure as claimed in claim 1, wherein the fixture element is made of one of a metal and a thermo-plastic polymer.

7. The adjustable fixture structure as claimed in claim 1, wherein the adjustable sliding trough has a shape selected from a group consisting of a trapezoid having a neck portion, a rectangular having a neck portion, a circle having a neck portion and a diamond having a neck portion.

8. The adjustable fixture structure as claimed in claim 1, wherein the connection mating portion has a shape selected from a group consisting of a trapezoid having a neck portion, a rectangular having a neck portion, a circle having a neck portion and a diamond having a neck portion.

9. The adjustable fixture structure as claimed in claim 1, wherein the fixture sliding trough has a shape selected from a group consisting of a trapezoid having a neck portion, a rectangular having a neck portion, a circle having a neck portion and a diamond having a neck portion.

10. The adjustable fixture structure as claimed in claim 1, wherein the fixture mating portion has a shape selected from a group consisting of a trapezoid having a neck portion, a rectangular having a neck portion, a circle having a neck portion and a diamond having a neck portion.

* * * * *